(12) United States Patent
Latterell et al.

(10) Patent No.: US 7,204,835 B2
(45) Date of Patent: Apr. 17, 2007

(54) SURGICAL INSTRUMENT

(75) Inventors: Scott T. Latterell, Minneapolis, MN (US); Douglas S. Wahnschaffe, Otsego, MN (US); Scott R. Sanders, Longmont, CO (US); Nigel Mark Goble, Stype (GB); Colin Charles Owen Goble, Englefield Green Egham (GB)

(73) Assignee: Gyrus Medical, Inc., Maple Grove, MN (US)

( * ) Notice: Subject to any disclaimer, the term of this patent is extended or adjusted under 35 U.S.C. 154(b) by 438 days.

(21) Appl. No.: 10/770,133

(22) Filed: Feb. 2, 2004

(65) Prior Publication Data

US 2005/0171533 A1 Aug. 4, 2005

(51) Int. Cl.
*A61B 18/14* (2006.01)

(52) U.S. Cl. .................... 606/48; 606/45; 606/50; 606/51; 606/52

(58) Field of Classification Search .............. 606/45, 606/48, 51–52
See application file for complete search history.

(56) References Cited

U.S. PATENT DOCUMENTS

| | | | | |
|---|---|---|---|---|
| 4,655,216 A | * | 4/1987 | Tischer | 606/51 |
| 5,160,334 A | * | 11/1992 | Billings et al. | 606/34 |
| 5,190,541 A | * | 3/1993 | Abele et al. | 606/46 |
| 5,258,006 A | * | 11/1993 | Rydell et al. | 606/205 |
| 5,342,381 A | * | 8/1994 | Tidemand | 606/174 |
| 5,443,463 A | * | 8/1995 | Stern et al. | 606/51 |
| 5,445,638 A | * | 8/1995 | Rydell et al. | 606/51 |
| 5,527,313 A | * | 6/1996 | Scott et al. | 606/51 |
| 5,599,350 A | * | 2/1997 | Schulze et al. | 606/51 |
| 5,665,085 A | * | 9/1997 | Nardella | 606/41 |
| 5,902,301 A | * | 5/1999 | Olig | 606/48 |
| 6,174,309 B1 | * | 1/2001 | Wrublewski et al. | 606/45 |
| 6,270,497 B1 | | 8/2001 | Sekino et al. | |

(Continued)

FOREIGN PATENT DOCUMENTS

EP 0 797 959 A 1/1997

(Continued)

*Primary Examiner*—Michael Peffley
*Assistant Examiner*—Alex Toy
(74) *Attorney, Agent, or Firm*—Nikolai & Mersereau, P.A.; Thomas J. Nikolai (57) ABSTRACT

A bipolar electrosurgical instrument comprises a handle (5), a body (1) joined to the handle, and a jaw assembly (12) joined to the body and arranged such that manipulation of the handle allows the opposed jaws of the jaw assembly to be opened and closed with respect to one another. A first of said opposed jaws (14) has at least a first coagulating electrode, and the other of said opposed jaws (13) has at least a second coagulating electrode and a cutting electrode (16) separated from the second coagulating electrode by an insulating member (17). The instrument is manipulated at the surgical site such that the jaws of the jaw assembly (12) are open with respect to one another, with the cutting electrode (16) and at least one of the first and second coagulating electrodes contacting tissue at the surgical site. A radio frequency electrosurgical signal is supplied between the cutting electrode and the at least one coagulating electrode, and the electrosurgical instrument is moved while maintaining the jaws (13, 14) in their open position so as to cut tissue at the surgical site.

8 Claims, 6 Drawing Sheets

U.S. PATENT DOCUMENTS

| | | |
|---|---|---|
| 6,273,887 B1 * | 8/2001 | Yamauchi et al. ............ 606/48 |
| 6,277,114 B1 * | 8/2001 | Bullivant et al. ............. 606/41 |
| 6,334,860 B1 | 1/2002 | Dorn |
| 6,554,829 B2 | 4/2003 | Schulze et al. |
| 6,676,660 B2 * | 1/2004 | Wampler et al. .............. 606/51 |
| 6,908,463 B2 | 6/2005 | Treat et al. |
| 2002/0198525 A1 | 12/2002 | Schulze et al. |
| 2003/0139741 A1 | 7/2003 | Goble et al. |
| 2004/0006340 A1 | 1/2004 | Latterell et al. |

FOREIGN PATENT DOCUMENTS

| | | |
|---|---|---|
| EP | 1287788 A | 8/2001 |
| WO | WO97/05829 A | 2/1997 |

* cited by examiner

SURGICAL INSTRUMENT

BACKGROUND OF THE INVENTION

1. Field of the Invention

This invention relates to a method of electrosurgically cutting tissue, and to an electrosurgical system for cutting tissue.

2. Discussion of the Prior Art

Electrosurgical cutting forceps are a commonly used tool in electrosurgery. U.S. Pat. No. 5,445,638 is a typical example, in which a pair of jaws are used to grip and coagulate tissue, and then a mechanical cutting blade moves between the jaws in order to cut the tissue. U.S. Pat. No. 6,554,829 is a more recent version of this type of instrument, still employing a pair of jaws and a mechanical cutting blade.

An alternative form of cutting forceps uses an electrosurgical cutting member as opposed to a mechanical cutting member. U.S. Pat. No. 6,174,309 is one such example, in which tissue is grasped between jaws, and then an electrosurgical cutting voltage is supplied to a cutting member located on one of the jaws. In all of these devices, the amount of tissue able to be cut is limited by the size of the jaws used to grasp the tissue while it is being cut.

The present invention attempts to provide an improvement over these prior art cutting devices, especially in that the cutting of relatively larger amounts of tissue is facilitated.

SUMMARY OF THE INVENTION

Accordingly, the invention provides a method of electrosurgically cutting tissue at a surgical site comprising the steps of (i) providing a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode separated from the second coagulating electrode by an insulating member, (ii) manipulating the electrosurgical instrument at the surgical site such that the jaws of the jaw assembly are open with respect to one another, with the cutting electrode and at least one of the first and second coagulating electrodes contacting tissue at the surgical site, (iii) supplying a radio frequency electrosurgical signal between the cutting electrode and the at least one coagulating electrode, and (iv) moving the electrosurgical instrument while maintaining the jaws in their open position so as to cut tissue at the surgical site.

Unlike the prior art devices, in which only tissue grasped between the jaws is cut, the present method moves the instrument with its jaws in the "open" position in order to cause tissue cutting. Preferably the electrosurgical instrument has a longitudinal axis and the instrument is moved longitudinally along said axis in order to cut tissue at the surgical site. Conveniently the first jaw has an inner face opposite the second jaw, and the cutting electrode is positioned on the inner face of the first jaw. In one convenient arrangement, the cutting electrode comprises a longitudinally extending rail.

The method of the present invention also allows the electrosurgical instrument to be used to coagulate as well as cut tissue. Accordingly, the method includes the additional steps of manipulating the handle in order to close the jaw assembly such that tissue at the surgical site is grasped therebetween, and supplying a radio frequency electrosurgical signal between the first and second coagulating electrodes so as to cause the coagulation of the tissue grasped between the jaws. In one arrangement the coagulation step is carried out following the movement of the instrument in order to cut tissue at the surgical site. In this way, the instrument can be used in order to control any bleeding caused by the cutting of the tissue.

Alternatively, the method includes the step of supplying a combined radio frequency signal consisting of a first cutting RF signal and a second coagulating RF signal, the first RF cutting signal being delivered between the cutting electrode and the at least one coagulating electrode, and the second coagulating RF signal being delivered between the first and second coagulating electrodes. In this way, the instrument is capable of simultaneously delivering a coagulating signal to the tissue as the tissue is being cut by the movement of the instrument. In a preferred arrangement, the combined radio frequency signal comprises a signal alternating constantly between the first cutting RF signal and the second coagulating RF signal so that the two are interleaved. There may also conveniently be provided adjustment means for varying the ratio of the blend mode so as to vary that part of the blend signal that is the first RF cutting signal as compared with the part of the blend signal that is the second RF coagulating signal. The adjustment means is conveniently operable by the user of the electrosurgical instrument, but can alternatively be automatically adjusted in response to feedback from one or more sensors detecting a parameter of the tissue, such as electrical impedance.

By the terms "RF cutting signal" and "RF coagulating signal" there is hereby meant any RF signal capable of cutting or coagulating tissue respectively. For example the signals may differ with respect to their voltage, the RF cutting signal having a higher voltage such that it is capable of cutting tissue, whereas the RF coagulating signal having a relatively lower voltage such that it is capable of coagulating but not cutting tissue. Additionally or alternatively, the RF cutting signal may differ from the RF coagulating signal in terms of its waveform rather than voltage. For example the RF coagulating signal may comprise shorter bursts of the same signal used for the cutting of tissue.

Where the terms "coagulate" or "coagulating" are used, there is hereby meant the prevention of bleeding following a tissue-cutting operation, as well as a process in which the collagen within tissue is made viscous so as to prevent blood flow through a blood vessel, for example prior to cutting. The terms are also herein meant to include vessel sealing, in which the walls of the vessel are fused together in order to seal the vessel.

The invention further resides in an electrosurgical system comprising (i) a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode separated from the second coagulating electrode by an insulating member, and (ii) an electrosurgical generator comprising one or more sources of RF output power, a controller operable to control the generator such that it is capable of providing a first cutting RF signal to the electrosurgical instrument or a second coagulating RF signal to the electrosurgical instrument, and, in a combined mode, to deliver both first and second RF signals, the signals being fed to the electrosurgical instrument such that, in the combined mode, the cutting signal is delivered between the cutting electrode and at least one of the first and second coagulating electrodes, and the coagulating RF signal is delivered between the first and second coagulating electrodes.

As described in our co-pending UK patent application 0305018.4, the generator may comprise a single RF source so that in the combined mode the generator system alternates constantly between delivering the cutting and coagulating signals. Alternatively, the generator comprises first and second RF sources operating at different frequencies, so as to deliver the cutting and coagulating signals simultaneously. As described in the patent application mentioned above, there is conceivably provided adjustment means for varying the ratio of the combined mode so as to vary that part of the combined signal that is the first RF cutting signal as compared with the part of the combined signal that is the second RF coagulating signal. Conveniently, the adjustment means is operable by the user of the electrosurgical instrument, but it may conceivably also be automatically adjusted in response to feedback from one or more sensors detecting a parameter of the tissue, such as the tissue impedance.

The invention also resides in a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode and separated from the second coagulating electrode by an insulating member, wherein the cutting electrode is in the form of a longitudinal rail mounted on the insulating member, the rail protruding from the insulating member by a distance of less than 100 microns. The dimensions of the rail have been found to be very important for ensuring that an effective electrosurgical cut occurs. Preferably the rail protrudes from the insulating member by a distance of between 25 and 75 microns, more preferably between 40 and 60 microns, and most preferably approximately 50 microns. Preferably, the width of the rail is between 25 and 75 microns, more preferably between 40 and 60 microns, and most preferably approximately 50 microns.

According to a further aspect of the invention, a method of electrosurgically cutting tissue at a surgical site comprises the steps of (i) providing a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode separated from the second coagulating electrode by an insulating member, p (ii) providing an electrosurgical generator comprising one or more sources of RF output power, a controller operable to control the generator such that it is capable of providing a first cutting RF signal to the electrosurgical instrument or a second coagulating RF signal to the electrosurgical instrument, and, in a combined mode, to deliver both first and second RF signals, the signals being fed to the electrosurgical instrument such that, in the combined mode, the cutting signal is delivered between the cutting electrode and at least one of the first and second coagulating electrodes, and the coagulating RF signal is delivered between the first and second coagulating electrodes, (iii) manipulating the electrosurgical instrument at the surgical site such that the jaws of the jaw assembly are open with respect to one another, (iv) closing the jaws of the jaw assembly such that tissue at the target site is contained therebetween, (v) supplying the combined radio frequency electrosurgical signal to the electrosurgical instrument from the electrosurgical generator, (vi) applying a first, relatively low, pressure to the tissue by the jaw assembly in order to cause the coagulation of the tissue held therebetween, and (vii) applying a second, relatively higher, pressure to the tissue by the jaw assembly in order to cause the cutting of the tissue.

DESCRIPTION OF THE DRAWINGS

The invention will now be further described, by way of example only, with reference to the accompanying drawings, in which.

DESCRIPTION OF THE PREFERRED EMBODIMENT

Figure 1:
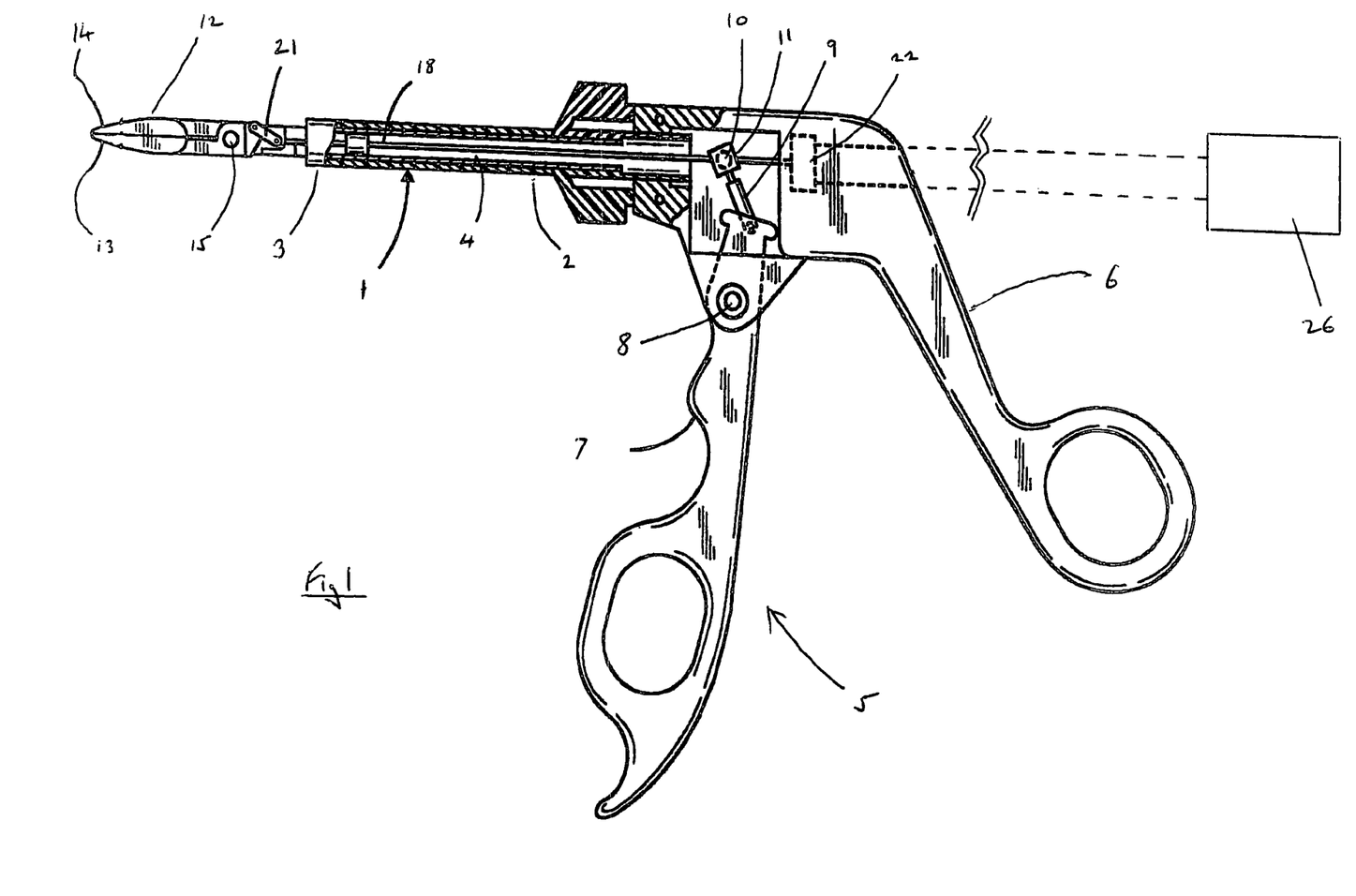
FIG. 1 is a schematic sectional view of an endoscopic electrosurgical instrument in accordance with the invention.

Referring to FIG. 1, a bipolar forceps device includes an elongated tubular shaft 1 with a proximal end 2, distal end 3, and a lumen 4 which extends for the entire length of the tubular member. At the proximal end 2 of the tubular member 1 is a scissors-type handle assembly 5 with a first handle 6 and a second handle 7. The second handle 7 is pivotable with respect to the first, about pivot pin 8. In a known design of actuation mechanism, the second handle 7 has a pin 9 affixed to the top thereof, such that movement of the handle causes a corresponding movement to a sphere 10 supported in a U-shaped cradle 11.

Figure 2:
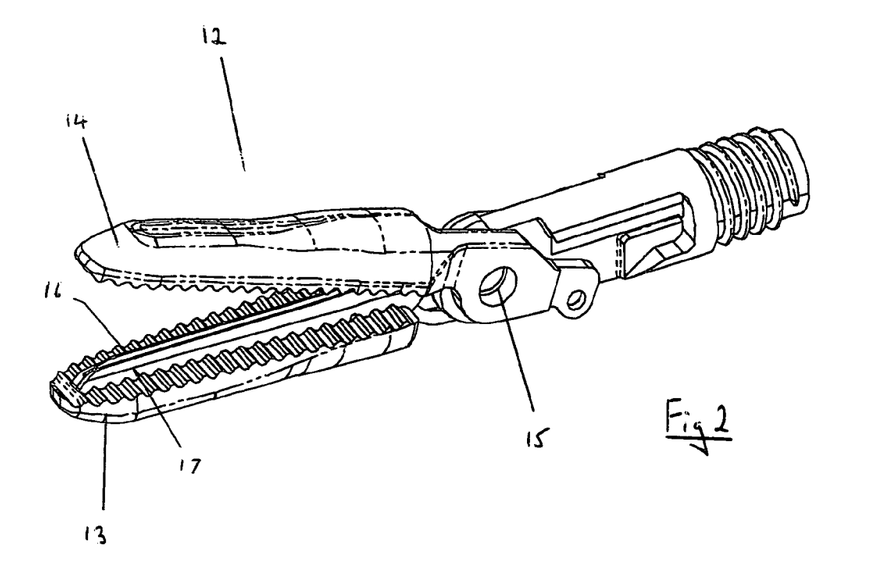
FIG. 2 is a perspective view of the jaw assembly of the instrument of FIG. 1.
Figure 3:
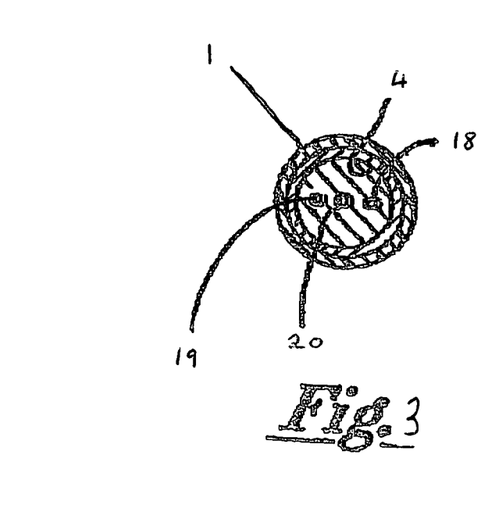
FIG. 3 is a cross-sectional view of the body of the instrument of FIG. 1.
Figure 5:
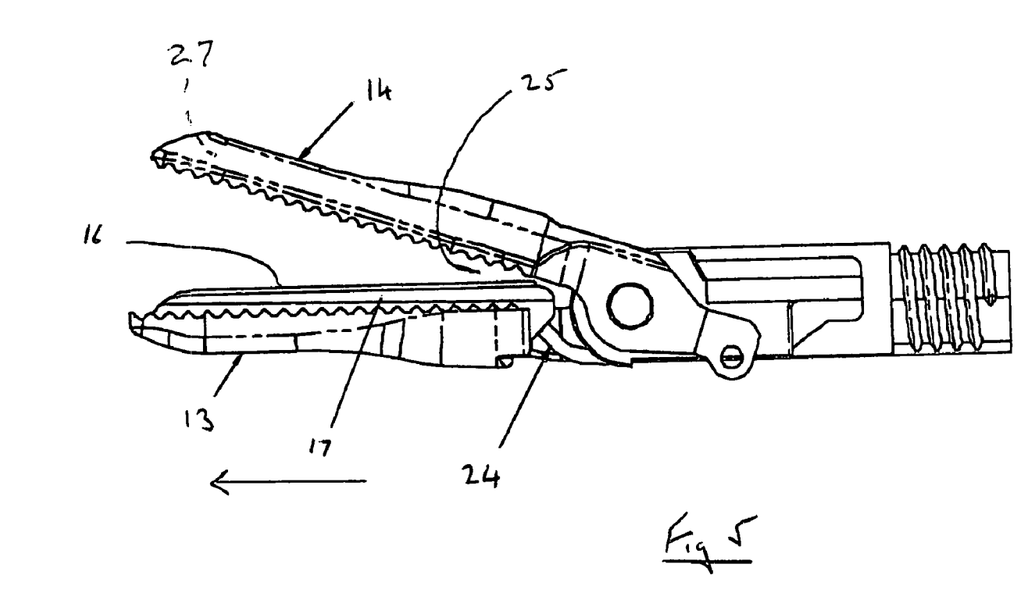
FIG. 5 is a side view of the jaw assembly of FIG. 2.

Fitted into the distal end 3 of the tubular member 1 is a forceps jaw assembly 12, more particularly shown in FIG. 2. The jaw assembly 12 comprises a first jaw member 13 and a second jaw member 14, pivotally joined to each other by an insulated rivet 15. Jaw member 13 is provided with a relatively long, but narrow cutting electrode 16 that is isolated from jaw member 13 by a ceramic insulator strip 17 that supports the cutting electrode. As shown in FIG. 3, three generally rigid electrically conductive rods 18, 19 and 20, each covered with a layer of electrical insulation, extend through the lumen 4 of the tubular member 1. The rods 18, 19 are pivotally connected to the respective jaw members 13, 14 by rigid links 21, whilst rod 20 is connected by means of a wire 24 (as best shown in FIG. 5) to the cutting electrode 16. The proximal ends of the rods 18, 19 and 20 extend from the tubular member through the sphere 10 and terminate in a connector 22, by which means the device can be attached to an electrosurgical generator 26.

Figure 4:
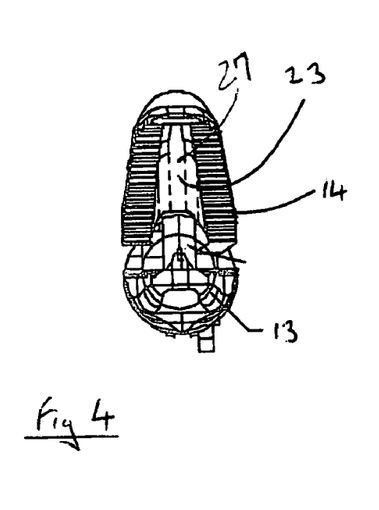
FIG. 4 is an end view of the jaw assembly of FIG. 2.

As shown in FIG. 2, the cutting electrode 16 is in the form of an elongate metal rail, extending along the length of the jaw member 13. The rail 16 is mounted atop the ceramic insulator 17 such that it is insulated from the conductive jaw member 13. The rail 16 is typically 50 to 100 microns in width, and protrudes from the ceramic insulator 17 by a distance of approximately 50 microns. When the jaw assembly 12 is in its closed position, the rail 16 is received in a corresponding longitudinal recess 23 in the jaw member 14, best shown in FIG. 4. A compressible strip 27 of insulting material is provided in the recess 23.

The operation of the device will now be further described. When tissue is to be cut, the jaw assembly 12 is brought adjacent the tissue to be cut, with the jaw assembly in its open position and the tissue positioned in the nip 25 of the jaw assembly. A cutting signal from the electrosurgical generator 26 is supplied, via the rod 20, to the cutting electrode 16, and the forceps device is moved longitudinally in the direction of the arrow shown in FIG. 5. Tissue bridging the cutting electrode 16 and one or both of the jaw members 13 and 14 is severed by the electrosurgical signal as the device is translated longitudinally, thereby forming a continuously progressing longitudinal cut line in the tissue. The jaw assembly is maintained in its open position throughout this process, defining the nip 25 in which the tissue is constrained.

The device can also be used to coagulate tissue, in a more conventional manner, using the jaw assembly in its closed position. The jaw assembly is closed, capturing tissue between the jaw member 13 and the jaw member 14. The cutting rail 16 is received in the recess 23 and, without the electrosurgical cutting signal previously described, does not have a cutting effect on the tissue therebetween. A coagulating signal from the electrosurgical generator 26 is supplied between the jaw members 13 and 14, via rods 18 and 19. This causes the coagulation of the tissue held between the jaws.

Figure 6:
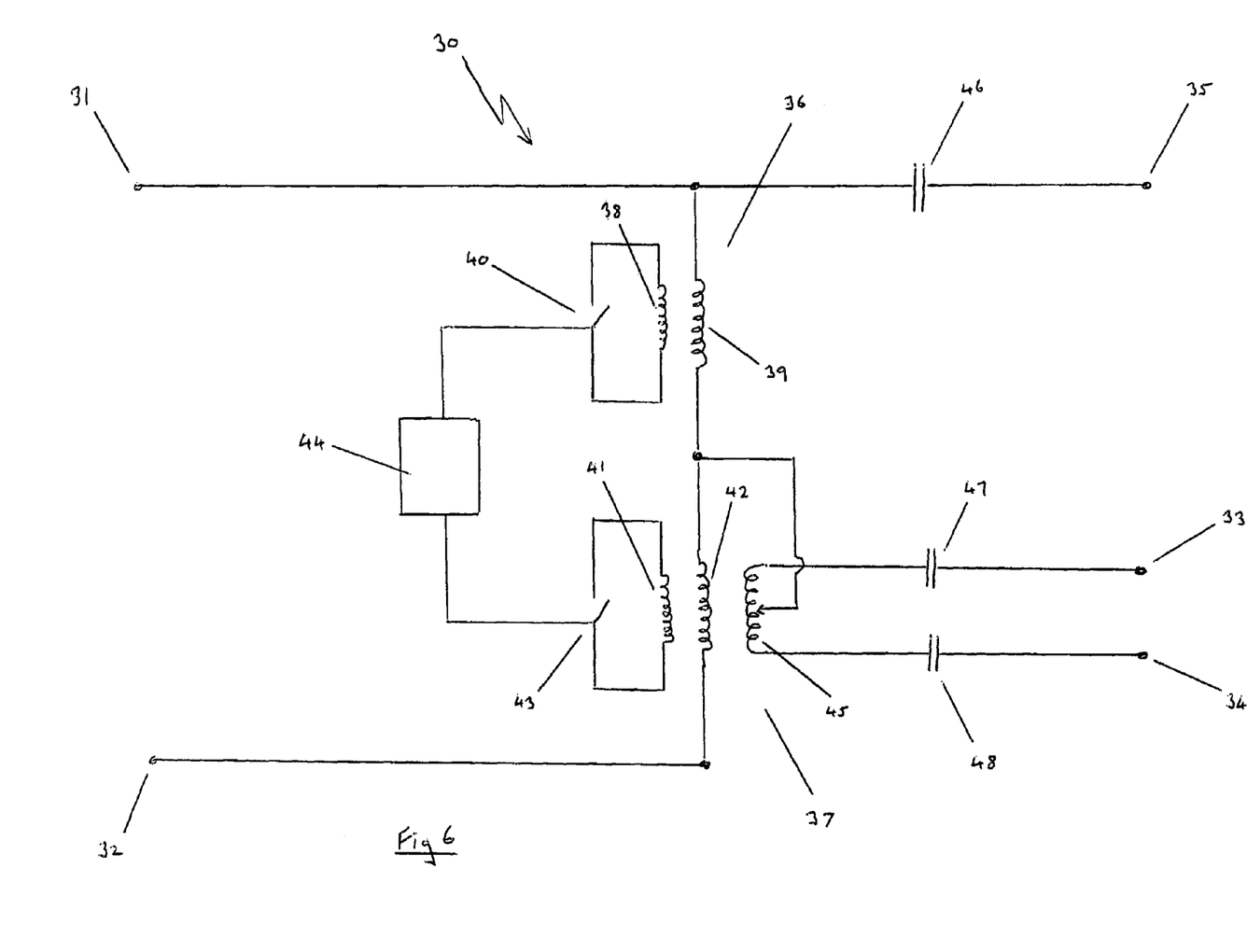
FIG. 6 is a circuit diagram of a switching circuit used in conjunction with the electrosurgical instrument of FIG. 1.

The device can also be used in a blended cutting and coagulation mode, as described in co-pending UK patent application 0305018.4. An example of an electrical circuit to provide such an arrangement is shown in FIG. 6. The circuit is shown generally at 30 and may be provided as a part of the output stage of the generator 26, as a part of the forceps instrument, or as a separate unit located between the generator and the instrument. Whichever arrangement is employed, input connections 31 and 32 are connected to the output of the generator 26, and output connections 33 and 34 to the rods 18 and 19, and, hence, to jaw members 13 and 14. Output connection 35 is connected to rod 20 and, hence, to the cutting electrode 16.

Between the input connections 31 and 32 there is a bridge circuit comprising a first transformer 36 and a second transformer 37. First transformer 36 comprises primary winding 38 and secondary winding 39. A switch element 40 is provided in parallel with primary winding 38. Second transformer 37 comprises primary winding 41 and secondary winding 42. A switch element 43 is provided in parallel with primary winding 41. Switch elements 40 and 43 are operated by control unit 44.

The second transformer 37 is a step-down transformer in which the secondary winding 42 is itself the primary to a further center-tapped secondary winding 45 connected across the output connections 33 and 34. Isolation capacitor 46 is provided between the bridge circuit and output connection 35, and isolation capacitors 47 and 48 between the bridge circuit and output connections 33 and 34.

The operation of the circuit is as follows. For a predetermined period, control unit 44 operates switch 43 to close and provide a short circuit across the primary winding 41 of the second transformer 37. In this arrangement, with the secondary transformer effectively short-circuited, the output of the generator is directed between the output connection 35 and both of the output connections 33 and 34. This has the effect of energizing the cutting rail 16 with a cutting voltage, as compared to the jaw members 13 and 14, which effectively act as return electrodes for the electrosurgical cutting operation.

After a predetermined period, the control unit 44 operates to open switch 43 and then close switch 40 to provide a short circuit across the primary winding 38 of the first transformer 36. There is a short predetermined delay between the opening of switch 43 and the closing of switch 40 to ensure that both switches are never closed at the same time (as this would provide a short circuit across the output connections of the generator 26). With switch 40 closed, the first transformer is effectively short-circuited, and the output of the generator is directed entirely to the second transformer 37. The second transformer is a step-down transformer, and provides a lower voltage signal between the output connections 33 and 34. This has the effect of energizing the first and second jaw members 13 and 14 with a coagulating voltage.

After a predetermined time, the control unit 44 opens switch 40 and then closes switch 43, reverting to the arrangement initially described in which a cutting voltage is delivered to the cutting rail 16. By constantly alternating between the two conditions herein described, the circuit provides a rapidly alternating cut and coagulation signal to a forceps device connected thereto. In this way, the forceps device is able to cut tissue as previously described, while simultaneously coagulating the tissue in order to curtail bleeding.

Although the forceps device of FIGS. 1 to 5 is shown as an endoscopic instrument, the invention can also be employed in connection with open instruments, as will be described with reference to FIGS. 7 to 10. The instrument shown generally at 50, comprises two longitudinal members 51 and 52, mounted for pivotal movement by means of pivot pin 53. The proximal end of member 51 is in the form of handle portion 54, and the proximal end of member 52 is in the form of handle portion 55. A ratchet mechanism 56 is provided on each handle portion for locking the handle portions when they are moved together into their closed position.

Figure 7:
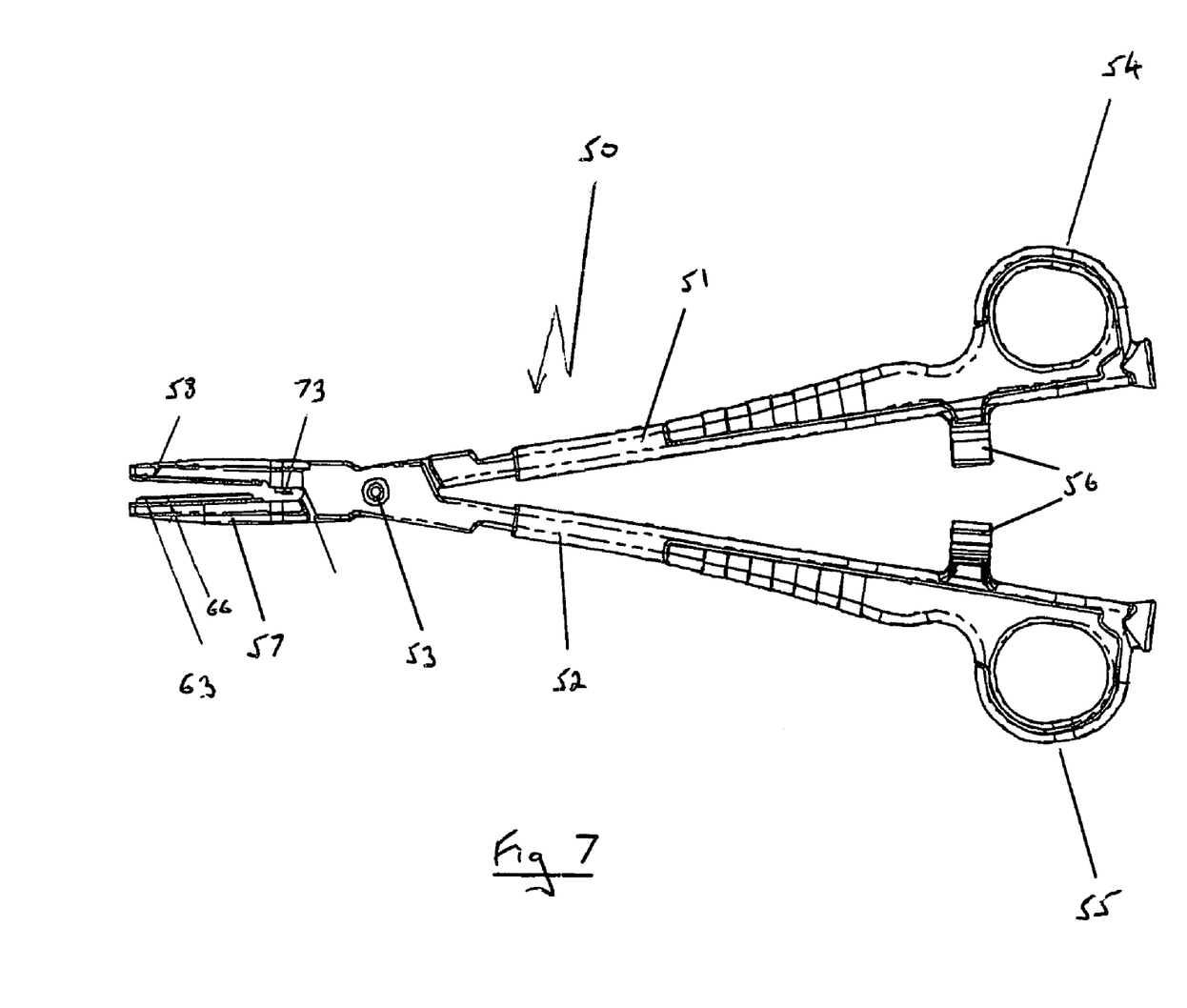
FIG. 7 is a schematic side view of an alternative embodiment of electrosurgical instrument for use in open procedures and constructed in accordance with the invention.

Distal of the pivot pin 53, the longitudinal member 51 forms a jaw member 57, while the longitudinal member 52 forms a jaw member 58. Movement of the handle portions 54 and 55 causes the jaw members 57 and 58 to open and close.

Figure 8:
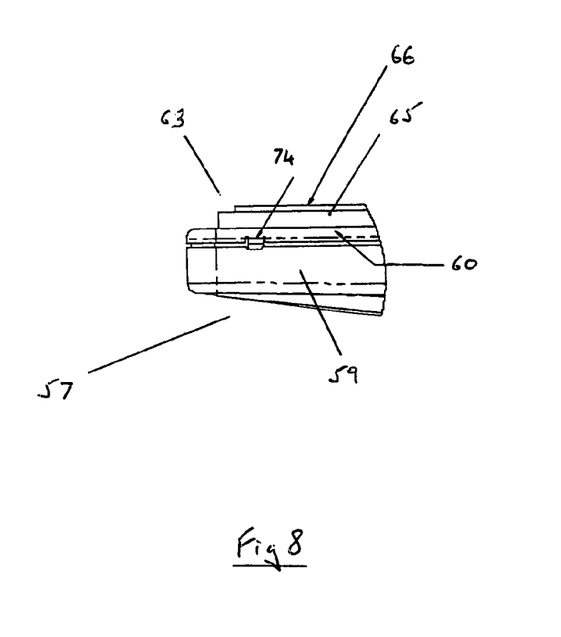
FIG. 8 is an enlarged view of a portion of one of the jaws of the instrument of FIG. 7.
Figure 9:
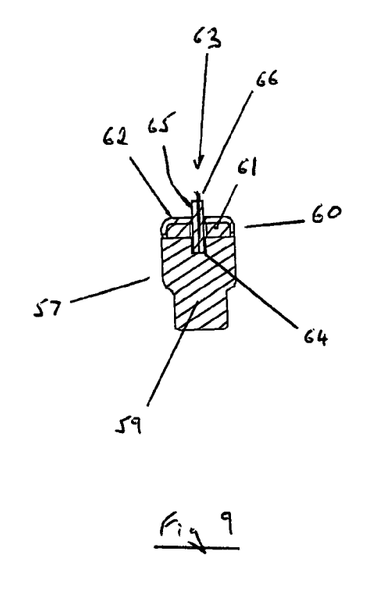
FIG. 9 is a sectional end view of one of the jaws of the instrument of FIG. 7.

With reference to FIGS. 8 and 9, the jaw member 57 comprises an integral base portion 59 on which is mounted a shim member 60, secured by means of clips 74. The shim member comprises an insulating strip 61, covered by a metallic surface electrode 62. A cutting electrode assembly 63 is mounted in a recess 64 running longitudinally along the jaw member 57. The cutting electrode assembly 63 comprises a raised insulator block 65, typically of a ceramic material, and a cutting electrode 66 mounted in a further longitudinal recess in the insulator block 65. The cutting electrode 66 is typically 100 microns in width, and protrudes from the insulator block 65 by a distance of approx 425 microns.

Figure 10:
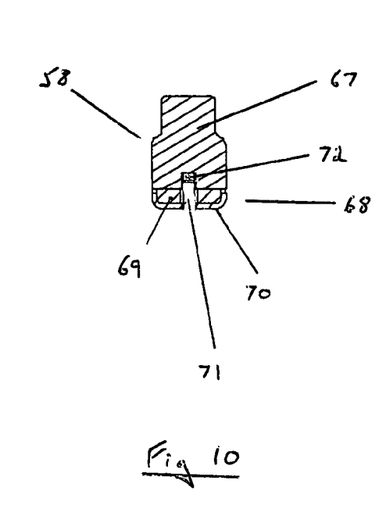
FIG. 10 is a sectional end view of the other jaw of the instrument of FIG. 7.

The opposite jaw member 58 shown in FIG. 10 also comprises a base portion 67 and a shim member 68. The shim member 68 also comprises an insulting strip 69, covered by a metallic surface electrode 70. The shim member 68 includes a central recess 71 in which the cutting electrode assembly 63 of the jaw member 57 can be received when the jaw members are in their closed position. At the base of the recess 71 is a strip 72 of resilient material such as an elastomer, such that the cutting electrode 66 bears against the strip 72 when the jaw members are closed one against the other. A stop member 73 (FIG. 7), mounted on one of the jaws, regulates the separation of the jaws when they are in their closed position. The operation of the instrument 50 will now be described. Firstly, the instrument can be used to cut tissue, as previously described. The jaw members 57 and 58 are held in their open position, and tissue is manoeuvred between the jaw members. An electrosurgical cutting signal is supplied to the cutting electrode 66, and the instrument 50 is moved longitudinally, thereby continuously severing tissue in a longitudinal cut line as the instrument is advanced. The surface electrodes 62 and 70 act as return electrodes for the electrosurgical cutting signal.

In a second technique, tissue can be cut using a 2-step process. The jaw members 57 and 58 are moved to their closed position, gripping tissue to be cut therebetween. Then a first coagulating RF signal is supplied between the surface electrodes 62 and 70, causing the coagulation of the tissue held between the jaw members. Without releasing the tissue, a second cutting RF signal is then supplied to the cutting electrode 66, causing the cutting of the tissue held by the jaw members.

Finally in a further technique, tissue can be coagulated and or cut using a process employing a blended signal as described with reference to FIG. 6. In this arrangement, a signal constantly alternating between the RF coagulating signal and the RF cutting signal is supplied to the jaw members, the RF coagulating signal being supplied between the surface electrodes 62 and 70, and the RF cutting signal being supplied to the cutting electrode 66 and with electrodes 62 and 70 acting as the return. The effect of the alternating RF signal upon the tissue is determined by the pressure applied to the tissue by the jaw members 57 and 58. The user of the instrument 50 closes the jaw members 57 and 58 to grip tissue therebetween. When the pressure applied by the jaws is at a first relatively low level, the predominant effect of the alternating RF signal is to cause the coagulation of the tissue held between the jaw members. When the user of the instrument wishes to sever the tissue held between the jaws, the user increases the pressure applied by the jaws to a second relatively higher level. At this relatively higher level of pressure, the predominant effect of the alternating RF signal is to cause the cutting of the tissue held between the jaw members 57 and 58. In this way, the user of the instrument 50 is able to switch between the coagulation and cutting of tissue merely by altering the pressure applied to the tissue by the jaw members.

The devices described herein can be used in a cutting technique in which tissue is cut, either with or without simultaneous coagulation, in which a forceps device is moved with its jaws held in an open condition, and in which a cutting rail acts to cut tissue as the device is moved in a longitudinal direction. Although suitable for both open and laparoscopic surgery, this technique is particularly advantageous in laparoscopic surgery, in which the excessive opening and closing of the jaws is to be avoided or is difficult to achieve. Also described are techniques for coagulating and cutting tissue in a 2-step process, in which the tissue is first coagulated and then severed with the jaws maintained in a closed position. One technique employs the pressure exerted by the jaws to regulate whether the effect of the instrument is primarily that of tissue coagulation or cutting.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of electrosurgically cutting tissue at a surgical site comprising the steps of
    (i) providing a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode mounted on one of the first and second jaws and separated from one of the first and second coagulating electrode by an insulating member,
    (ii) manipulating the electrosurgical instrument at the surgical site such that the jaws of the jaw assembly are open with respect to one another, with the cutting electrode and at least one of the first and second coagulating electrodes contacting tissue at the surgical site,
    (iii) supplying a radio frequency electrosurgical signal between the cutting electrode and the at least one of the first and second coagulating electrode, and
    (iv) moving the electrosurgical instrument while maintaining the jaws in their open position and with the cutting electrode remaining stationary relative to the jaw on which it is mounted so as to cut tissue at the surgical site.

2. A method of electrosurgically cutting tissue according to claim 1 wherein the first jaw has an inner face opposite the second jaw, and the cutting electrode is positioned on the inner face of the first jaw.

3. A method of electrosurgically cutting tissue according to claim 1 wherein the electrosurgical instrument has a longitudinal axis and the instrument is moved longitudinally along said axis in order to cut tissue at the surgical site.

4. A method of electrosurgically cutting tissue according to claim 3 wherein the cutting electrode comprises a longitudinally extending rail.

5. A method of electrosurgically cutting tissue according to claim 1 including the additional steps of manipulating the handle in order to close the jaw assembly such that tissue at the surgical site is grasped therebetween, and supplying a radio frequency electrosurgical signal between the first and second coagulating electrodes so as to cause the coagulation of the tissue grasped between the jaws.

6. A method of electrosurgically cutting tissue according to claim 5 wherein the additional steps are carried out following the movement of the instrument in order to cut tissue at the surgical site.

7. A method of electrosurgically cutting tissue according to claim 1 including the step of supplying a combined radio frequency signal consisting of a first cutting RF signal and a second coagulating RF signal, the first RF cutting signal being delivered between the cutting electrode and the at least one coagulating electrode, and the second coagulating RF signal being delivered between the first and second coagulating electrodes.

8. A method of electrosurgically cutting tissue according to claim 7 wherein the combined radio frequency signal comprises a signal alternating between the first cutting RF signal and the second coagulating RF signal.

* * * * *